(12) United States Patent
Jackson

(10) Patent No.: US 9,867,730 B2
(45) Date of Patent: Jan. 16, 2018

(54) TUBING VALVE AND USES THEREOF

(71) Applicant: FlowSense Ltd., M.P. Misgav (IL)

(72) Inventor: Martin Clive Henry Jackson, Ginot Shomron (IL)

(73) Assignee: FLOWSENSE LTD., M.P. Misgav (IL)

( * ) Notice: Subject to any disclaimer, the term of this patent is extended or adjusted under 35 U.S.C. 154(b) by 391 days.

(21) Appl. No.: 14/405,494

(22) PCT Filed: Jun. 12, 2013

(86) PCT No.: PCT/IL2013/050501
§ 371 (c)(1),
(2) Date: Dec. 4, 2014

(87) PCT Pub. No.: WO2013/186776
PCT Pub. Date: Dec. 19, 2013

(65) Prior Publication Data
US 2015/0173937 A1 Jun. 25, 2015

Related U.S. Application Data

(60) Provisional application No. 61/658,462, filed on Jun. 12, 2012.

(51) Int. Cl.
*A61F 5/44* (2006.01)
*A61F 5/451* (2006.01)
(Continued)

(52) U.S. Cl.
CPC ............ *A61F 5/4405* (2013.01); *A61F 5/451* (2013.01); *A61M 39/10* (2013.01); *A61M 39/12* (2013.01); *F16L 37/40* (2013.01); *A61J 1/10* (2013.01); *A61J 1/1412* (2013.01); *A61M 5/162* (2013.01); *A61M 39/26* (2013.01)

(58) Field of Classification Search
CPC . A61F 5/4405; A61F 5/451; A61J 1/10; A61J 1/1412; A61M 39/10; A61M 39/12; A61M 39/26; A61M 5/162; F16L 37/40; F16L 37/00; F16L 37/006; F16K 21/04; F16K 21/06; F16K 21/14; F16K 23/00;
(Continued)

(56) References Cited

U.S. PATENT DOCUMENTS 3,260,120 A * 7/1966 Stilwell ............... G01N 1/20
73/863.54
4,625,570 A * 12/1986 Witherspoon ........ G01N 1/20
73/863.81

(Continued)

OTHER PUBLICATIONS

European Search Report from Corresponding European Patent Application No. EP 13804413.6, dated Feb. 4, 2016.

*Primary Examiner* — Adam Marcetich
(74) *Attorney, Agent, or Firm* — Greer, Burns & Crain, Ltd.

(57) ABSTRACT

A tubing valve is provided, including a valve body; a valve stem configured to be inserted into the valve body; and a valve tip configured to be inserted and fixed into the valve stem on its top part after it is positioned inside the valve body and to provide a holding position to a tube on its bottom side, wherein the tubing valve is opened upon pushing the valve tip and closed upon pulling said tube off the valve tip.

10 Claims, 8 Drawing Sheets

(51) Int. Cl.
*A61M 39/00* (2006.01)
*A61M 39/26* (2006.01)
*A61M 39/10* (2006.01)
*A61M 39/12* (2006.01)
*F16L 37/40* (2006.01)
*A61M 5/162* (2006.01)
*A61J 1/10* (2006.01)
*A61J 1/14* (2006.01)

(58) Field of Classification Search
CPC ...... F16K 35/02; F16K 35/022; F16K 35/025;
F16K 35/027
See application file for complete search history.

(56) References Cited

U.S. PATENT DOCUMENTS

| | | | |
|---|---|---|---|
| 4,629,159 A | 12/1986 | Wellenstam | |
| 5,509,433 A | 4/1996 | Paradis | |
| 5,820,614 A | 10/1998 | Erskine et al. | |
| 6,220,570 B1 * | 4/2001 | Heinrichs | F16L 37/40 |
| | | | 251/149.1 |
| 7,150,740 B2 | 12/2006 | Bennett et al. | |
| 8,240,335 B1 * | 8/2012 | Broberg | F16K 11/0716 |
| | | | 123/DIG. 3 |
| 2002/0189684 A1 * | 12/2002 | Williamson | A47G 21/185 |
| | | | 137/510 |
| 2005/0132821 A1 * | 6/2005 | Furey | G01N 1/10 |
| | | | 73/863.31 |
| 2006/0079850 A1 * | 4/2006 | Adams | A61M 25/02 |
| | | | 604/284 |
| 2007/0043334 A1 | 2/2007 | Guala | |
| 2007/0102450 A1 * | 5/2007 | Stiers | B01F 11/04 |
| | | | 222/181.1 |
| 2009/0229671 A1 * | 9/2009 | Hartnett | A61M 39/22 |
| | | | 137/13 |
| 2009/0274566 A1 * | 11/2009 | Fong | F04B 53/1032 |
| | | | 417/307 |
| 2009/0314101 A1 | 12/2009 | Levine | |
| 2010/0158759 A1 * | 6/2010 | Olivier | G01N 1/18 |
| | | | 422/400 |
| 2010/0286667 A1 | 11/2010 | Paz | |
| 2011/0233210 A1 * | 9/2011 | Fatherazi | B01J 19/0053 |
| | | | 220/254.9 |
| 2011/0251572 A1 | 10/2011 | Nishtala et al. | |
| 2011/0282311 A1 | 11/2011 | Nishtala | |
| 2013/0167960 A1 * | 7/2013 | Pethe | F17C 13/00 |
| | | | 137/798 |

* cited by examiner

TUBING VALVE AND USES THEREOF

BACKGROUND

The present invention relates generally to a novel tubing valve that may be used in low and medium pressure applications in general, and in particular to a novel medical valve that may be used for example in systems for removal of urine from catheterized patients to thereby allow avoiding any contact with the patient's urine.

There are many situations in which a medical team needs to engage with liquids secretion systems as well as with diagnostic and therapeutic systems that require replacement of disposable collecting bags that contain liquids. Such engagement usually results in leakage of liquids that contaminates both the near surroundings, and the hands of the medical team with liquids such as urine, blood, or other toxic and cytotoxic matter.

SUMMARY

The present invention, in at least some embodiments is directed to a novel tubing valve which is particularly applicable to medical uses. For medical uses, the medical tubing valve may optionally be used for urine collection systems, for example to permit a collecting bag that is in use to be removed and to be replaced by a fresh bag, while preventing any contact between the medical team performing the replacement and the liquids in the collecting bag, and therefore keeping the near surrounding and medical staff clean.

According to at least some embodiments of the present invention, there are provided hygienic systems and methods for collecting urine from a patient, wherein the systems comprise a novel medical tubing valve that functionally prevents direct contact between the medical team and the urine.

The valve may also optionally be used for non-medical applications, for example in situations where it is desirable to prevent contact with undesirable substances upon changing receptacles for such substances that are connected to tubing. These applications might include drawing off samples of corrosive fluid from a flow, checking fluid concentrations, checking fluid residue, or draining fluid residues in general.

According to at least some embodiments, there is provided a tubing valve, comprising: a valve body; a valve stem adapted to be inserted into the valve body where the valve stem has an inlet port; and a valve tip adapted to be inserted and fixed into the valve stem after a first end of the valve tip is positioned inside the valve body, wherein a second end of the valve tip is adapted to hold a tube, wherein the tubing valve is adapted to open upon attaching the tube to the valve tip, causing the valve stem to move away from the valve body and to permit fluid access to the inlet port, and is adapted to close upon removing the tube from the valve tip, causing the valve stem to move toward the valve body and to block fluid access to the inlet port.

Optionally the valve body further comprises a central bore, wherein the valve stem comprises a first portion having a greater area and a second portion having a smaller area, wherein a portion of the central bore is narrower than a second portion of the central bore, the narrower portion receiving the second portion of the valve stem and the second portion of the central bore receiving the first portion of the valve stem having the greater area.

Also optionally the first end of the valve tip contacts the second portion of the valve stem and causes the valve stem having the inlet port to move away from the valve body to open the valve.

Also optionally the second end of the valve tip is adapted to be inserted into the tube and is adapted to cause the first end of the valve tip to contact the second portion of the valve stem.

Also optionally the narrower portion of the central bore is adapted to be inserted into the tube with the second end of the valve tip, thereby preventing the valve from closing when the tube is attached to the valve.

Also optionally the second end of the valve tip is adapted to move away from the valve body upon removal of the tube and hence to cause the first end of the valve tip to cease to contact the second portion of the valve stem having the inlet port, thereby closing the valve.

Also optionally the valve stem and the central bore of the valve body each comprise complementary conical structures, such that when the tubing valve is closed, the conical structure of the valve stem having the inlet port is larger than the conical structure of the central bore, thereby blocking the inlet port.

According to at least some embodiments of the present invention, there is provided a tubing valve, comprising: a valve body having a flow control mechanism consisting essentially of a valve stem having an inlet port adapted to be inserted into the valve body and a valve tip adapted to be inserted and fixed into the valve stem after a first end of the valve tip is positioned inside the valve body, wherein a second end of the valve tip is adapted to hold a tube, wherein the tubing valve is opened upon attaching the tube to the valve tip, causing the valve stem to move away from the valve body and to permit fluid access to the inlet port, and closed upon removing the tube from the valve tip, causing the valve stem to move toward the valve body and to block fluid access to the inlet port.

Optionally the valve is adapted to be used in low and medium pressure applications.

Optionally the valve further comprises a medical tube attached to the valve.

Also optionally the valve is positioned in a urinary catheter system, and wherein the medical tube is a urine collecting bag tube.

According to at least some embodiments of the present invention there is provided an urinary catheter system comprising: a catheter for insertion to the patient, a urine collection bag, a urine collection bag tube, a tubing valve, and a tube having an inner diameter from four millimeters to six millimeters, the tube having an inner surface which is hydrophobic at least along a first segment thereof and being adapted to provide a continuously negative fluid pressure therein, the tube being connected to the catheter at one end of the tube, and the tube being connected to one end of the tubing valve at an opposite end of the tube, and the valve being connected to the urine collection bag tube at an opposite end of the valve such that the tube conveys a column of fluid held by a meniscus of the column of fluid from the catheter to the collection bag without interruption; wherein the valve is adapted to be open upon connecting the urine collection bag tube and the valve is adapted to be closed upon disconnecting the urine collection bag tube.

Optionally the system further comprises a drop counter, wherein at the opposite end of the tube, the tube is connected to the drop counter and the tubing valve is connected to the drop counter.

Also optionally the tubing valve comprises: a valve body adapted for connecting to the drop counter; a valve stem adapted to be inserted into the valve body where the valve stem has an inlet port; and a valve tip adapted to be inserted and fixed into the valve stem after a first end of the valve tip is positioned inside the valve body, wherein a second end of the valve tip is adapted to hold the urine collection bag tube, wherein the tubing valve is adapted to open upon attaching the urine collection bag tube to the valve tip, causing the valve stem and the inlet port to move away from the valve body and to permit fluid access to the inlet port, and is adapted to close upon removing the tube from the valve tip, causing the valve stem and the inlet port to move toward the valve body and to block fluid access to the inlet port.

Also optionally the valve body further comprises a central bore, wherein the valve stem comprises a first portion having a greater area and a second portion having a smaller area, wherein a portion of the central bore is narrower than a second portion of the central bore, the narrower portion receiving the second portion of the valve stem and the second portion of the central bore receiving the first portion of the valve stem having the greater area.

Also optionally the first end of the valve tip is adapted to contact the second portion of the valve stem and is adapted to cause the valve stem having the inlet port to move away from the valve body to open the valve.

Also optionally the second end of the valve tip is adapted to be inserted into the urine collection bag tube and is adapted to cause the first end of the valve tip to contact the second portion of the valve stem.

Also optionally the narrower portion of the central bore is adapted to be inserted into the urine collection bag tube with the second end of the valve tip, thereby preventing the valve from closing when the urine collection bag tube is attached to the valve.

Also optionally the second end of the valve tip is adapted to move away from the valve body upon removal of the urine collection bag tube and hence to cause the first end of the valve tip to cease to contact the second portion of the valve stem having the inlet port, thereby closing the valve.

Also optionally the valve stem and the central bore of the valve body each comprise complementary conical structures, such that when the tubing valve is closed, the conical structure of the valve stem having the inlet port is larger than the conical structure of the central bore, thereby blocking the inlet port.

According to at least some embodiments of the present invention there is provided a method for enhanced continuous flow of urine in a catheterized patient comprising: providing an arrangement comprising a hydrophobic tube having an inner diameter of from four to six millimeters, the tube having an inner surface which is hydrophobic at least along a first segment thereof and being arranged to provide a continuously negative fluid pressure therein; attaching the hydrophobic tube to the urinary catheter unit; attaching the hydrophobic tube to a drop counter inlet; attaching a drop counter outlet to a tubing valve, wherein the valve comprises: a valve body; a valve stem adapted to be inserted into the valve body where the valve stem has an inlet port; and a valve tip adapted to be inserted and fixed into the valve stem after a first end of the valve tip is positioned inside the valve body, wherein the hydrophobic tube is attached to a first end of the valve tip; attaching a second end of the valve tip to a urine collection bag tube, thereby causing the valve to open; connecting the collection bag tube to a urine collection bag, the catheter unit being adapted to continuously remove fluid from a bladder of the patient and to convey the fluid into the tube under a continuously negative fluid pressure; and conveying a column of fluid held by a meniscus of the column of fluid from the catheter to the collection bag via the valve without interruption, without manual manipulation of the tube or the collection bag, wherein a second end of the valve tip is adapted to hold the urine collection bag tube.

Also optionally the valve body further comprises a central bore, wherein the valve stem comprises a first portion having a greater area and a second portion having a smaller area, wherein a portion of the central bore is narrower than a second portion of the central bore, the narrower portion receiving the second portion of the valve stem and the second portion of the central bore receiving the first portion of the valve stem having the greater area.

Also optionally the first end of the valve tip contacts the second portion of the valve stem and causes the valve stem having the inlet port to move away from the valve body to open the valve.

Also optionally the second end of the valve tip is adapted to be inserted into the urine collection bag tube and is adapted to cause the first end of the valve tip to contact the second portion of the valve stem.

Also optionally the narrower portion of the central bore is adapted to be inserted into the urine collection bag tube with the second end of the valve tip, thereby preventing the valve from closing when the urine collection bag tube is attached to the valve.

Also optionally the second end of the valve tip is adapted to move away from the valve body upon removal of the urine collection bag tube and hence to cause the first end of the valve tip to cease to contact the second portion of the valve stem having the inlet port, thereby closing the valve.

Also optionally the valve stem and the central bore of the valve body each comprise complementary conical structures, such that when the tubing valve is closed, the conical structure of the valve stem having the inlet port is larger than the conical structure of the central bore, thereby blocking the inlet port.

According to at least some embodiments of the present invention, there is provided an urinary catheter system comprising: a catheter for insertion to the patient, a catheter tube, a tubing valve, and a urine collection bag having a urine collection bag tube, the catheter tube being connected to the catheter at one end of the tube, and the tube being connected to one end of the valve at an opposite end of the tube, and the valve being connected to the urine collection bag tube at an opposite end of the valve, wherein the tubing valve is adapted to permit fluid flow when the urine collection bag tube is connected and prevent fluid flow when the urine collection bag tube is removed.

Optionally the valve comprises: a valve body; a valve stem adapted to be inserted into the valve body where the valve stem has an inlet port; and a valve tip adapted to be inserted and fixed into the valve stem after a first end of the valve tip is positioned inside the valve body, wherein a second end of the valve tip is adapted to hold the urine collection bag tube.

Also optionally the valve body further comprises a central bore, wherein the valve stem comprises a first portion having a greater area and a second portion having a smaller area, wherein a portion of the central bore is narrower than a second portion of the central bore, the narrower portion receiving the second portion of the valve stem and the second portion of the central bore receiving the first portion of the valve stem having the greater area.

Also optionally the first end of the valve tip contacts the second portion of the valve stem and causes the valve stem having inlet port to move away from the valve body to open the valve.

Also optionally the second end of the valve tip is adapted to be inserted into the urine collection bag tube and is adapted to cause the first end of the valve tip to contact the second portion of the valve stem.

Also optionally the narrower portion of the central bore is adapted to be inserted into the urine collection bag tube with the second end of the valve tip, thereby preventing the valve from closing when the urine collection bag tube is attached to the valve.

Also optionally the second end of the valve tip is adapted to move away from the valve body upon removal of the urine collection bag tube and hence to cause the first end of the valve tip to cease to contact the second portion of the valve stem having the inlet port, thereby closing the valve.

Also optionally the valve stem and the central bore of the valve body each comprise complementary conical structures, such that when the tubing valve is closed, the conical structure of the valve stem having the inlet port is larger than the conical structure of the central bore, thereby blocking the inlet port.

BRIEF DESCRIPTION OF THE DRAWINGS

Examples illustrative of embodiments of the disclosure are described below with reference to figures attached hereto. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings.

The figures (Figs.) are listed below.

DETAILED DESCRIPTION

In the following description, various aspects of a novel tubing valve adapted for various applications in both low and medium pressure applications will be described. For the purpose of explanation, specific configurations and details are set forth in order to provide a thorough understanding of the apparatus.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below. The descriptions, examples and materials presented in the description, as well as in the claims, should not be construed as limiting, but rather as illustrative.

Terms for indicating relative direction or location, such as "right" and "left", "up" and "down", "top" and "bottom", "horizontal" and "vertical", "higher" and "lower", and the like, may also be used, without limitation.

Figure 1:
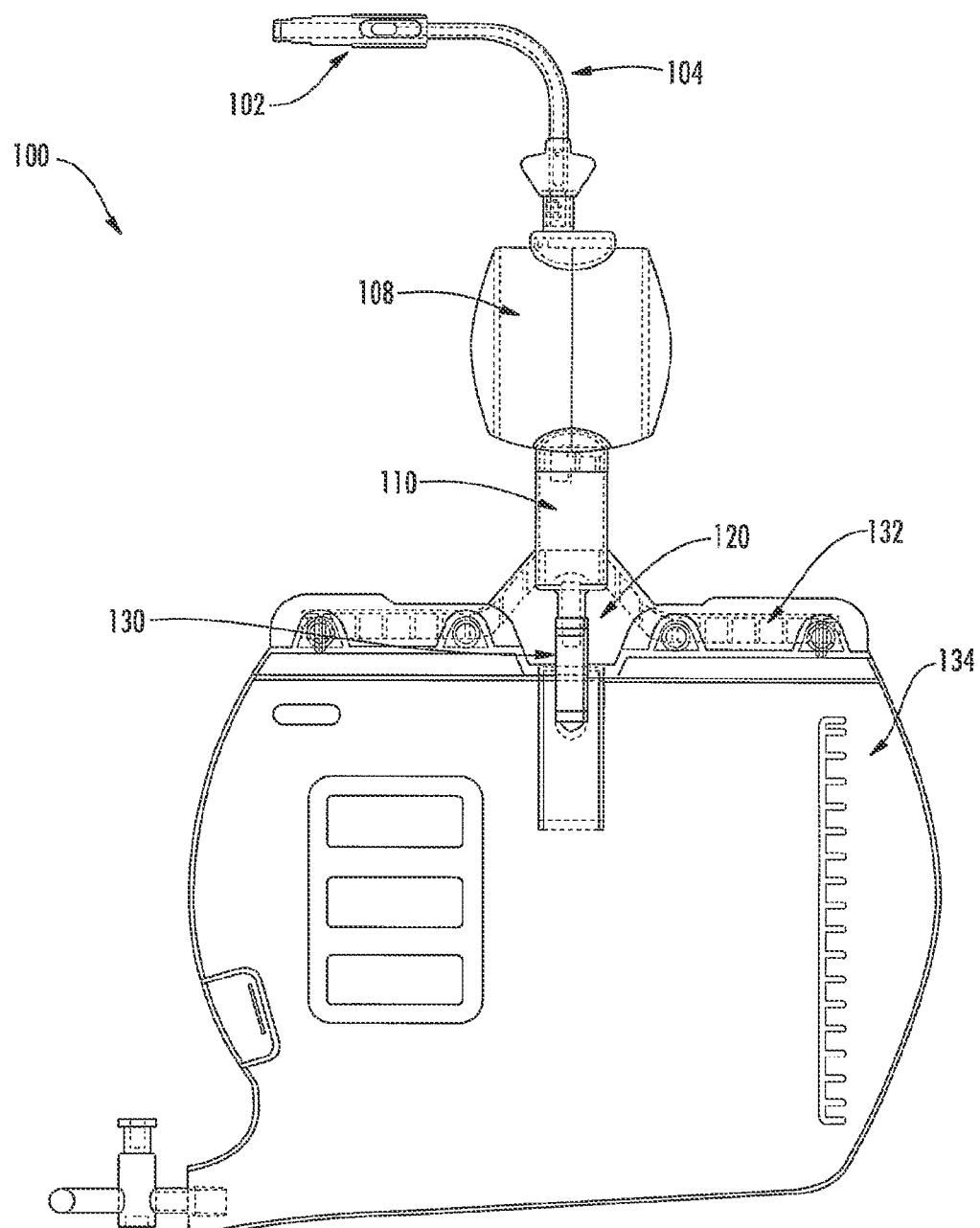
FIG. 1 is a schematic illustration showing a urinary catheterization kit including a valve in accordance with variations of the present invention.
Figure 2:
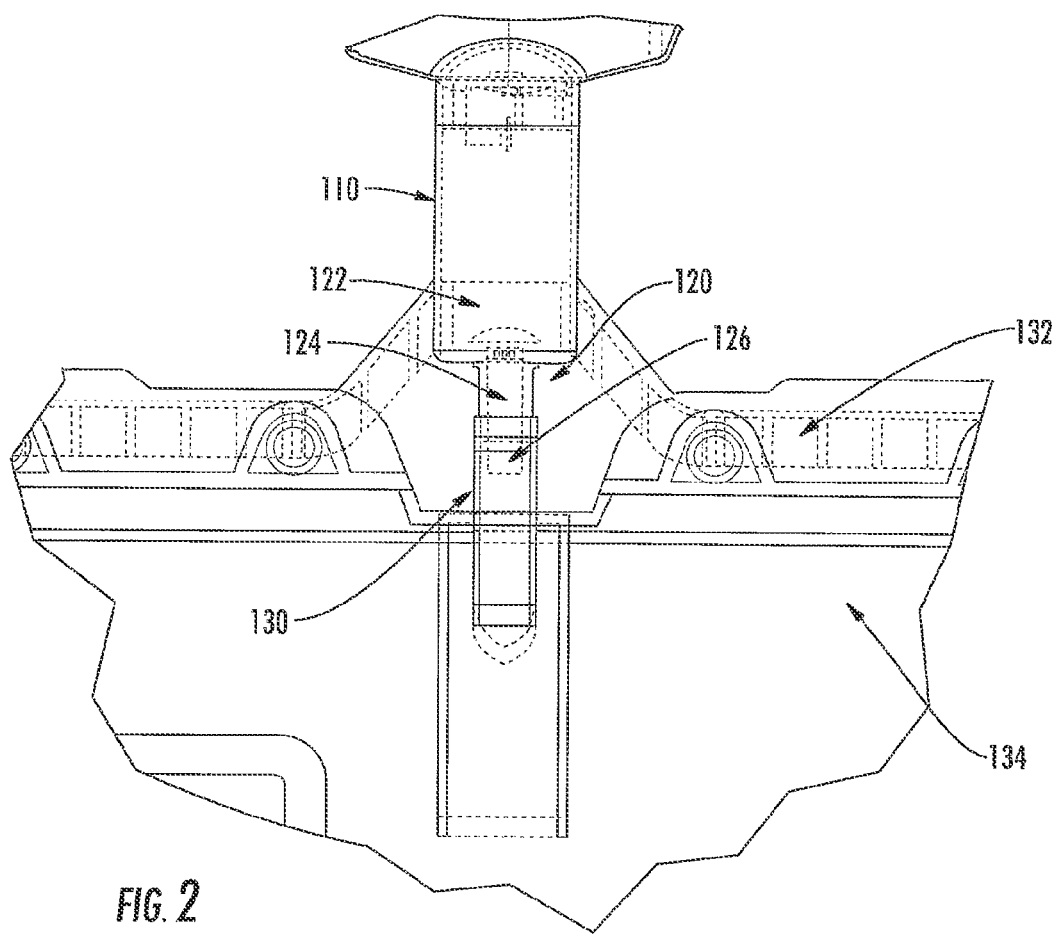
FIG. 2 shows a detail of FIG. 1 in accordance with variations of the present invention.

Reference is now made to FIGS. 1 and 2 that schematically illustrate a urinary catheterization kit 100 comprising a catheter 102, a catheterization tube 104, a receiving reservoir 108, drop chamber 110, the valve 120 of the present invention, a urine collecting bag attachment tube 130, and a means for attachment 132 of the kit 100 to a urine collection bag 134, in accordance with variations of the present invention. Valve 120 comprises valve body 122, valve stem 124 and valve tip 126 as will be described in more detail below.

In accordance with the variation illustrated in this figure, valve 120 is positioned between drop chamber 110 and attachment tube 130. The inlet of valve body 122 is preferably sized to allow the outlet of drop chamber 110 to be attached and held in place without the need for any retaining mechanism. In an optional embodiment with no retaining mechanism and an inlet diameter of up to 8 mm, the valve 120 will remain attached under medium or high pressures not exceeding approximately 4 bar.

The outlet of valve 120 is preferably sized to allow attachment tube 130 to be attached and held in place without the need for any retaining mechanism.

When used in a urinary catheterization system the closing as well as the opening of valve 120 is very intuitive and allows the removal and replacement of collection bag 134, while preventing any contact between the medical team performing the replacement and the liquids in the collection bag, therefore keeping the near surrounding and medical staff clean. When collection bag 134 with attachment tube 130 is detached or otherwise removed from valve 120, valve 120 is pulled close preventing the flow of liquid, and when collection bag 134 with tube 130 is pushed onto or otherwise connected to valve 120, valve 120 is pushed open allowing the flow of liquid. This mechanism will be described in more detail below.

In accordance with one preferred variation of the invention, the valve may be used in urinary catheter arrangements as illustrated in detail in U.S. Pat Application No. 2010/0286667 (hereinafter: "667') incorporated herein in its entirety by reference and owned in common with the present application. The arrangement shown in FIG. 1 is similar to the arrangements of the above reference and may optionally have the same or similar parameters as described below.

The arrangement illustrated in 667' is arranged for enhanced continuous flow of urine in a catheterized patient and for preventing urinary tract infections in the patient. The arrangement generally comprises a catheter tube with a hydrophobic inner surface that is preferably polished, having an inner diameter of four to six millimeters, the tube being arranged to provide a continuously negative fluid pressure of less than 50 cm equivalent of water therein as a result of a meniscus forming at the beginning of a flow of urine from the bladder of the patient as a result of the narrowness of the tube and the repulsion of the urine from the hydrophobic surfaces of the tube, whereby during operation, the tube is always full of urine. As a result, a natural negative pressure builds up in the tube which serves to continuously suction urine from the bladder in a closed system, keeping the bladder empty resulting in a steady flow which does not allow for air spaces and bacterial build-up in the tube in the area adjacent the bladder.

Since the continuous negative pressure means that the tube is always full of urine, medical stuff may have difficulties replacing the urine bag when it is full. Without wishing to be limited in any way, valve 120 provides a solution to this problem and to allow replacement of a urine bag, such as urine collection bag 134, or any other collected secreted fluids in a clean and sterile manner. When collection bag 134 with attachment tube 130 is detached from valve 120, valve 120 closes and no flow through valve 120 is possible. In addition, in use, valve 120 prevents direct human contact with the urine or with other biohazardous materials as there is no need to touch any other part other than attachment tube 130 of collection bag 134 when replacing collection bag 134.

Figure 3:
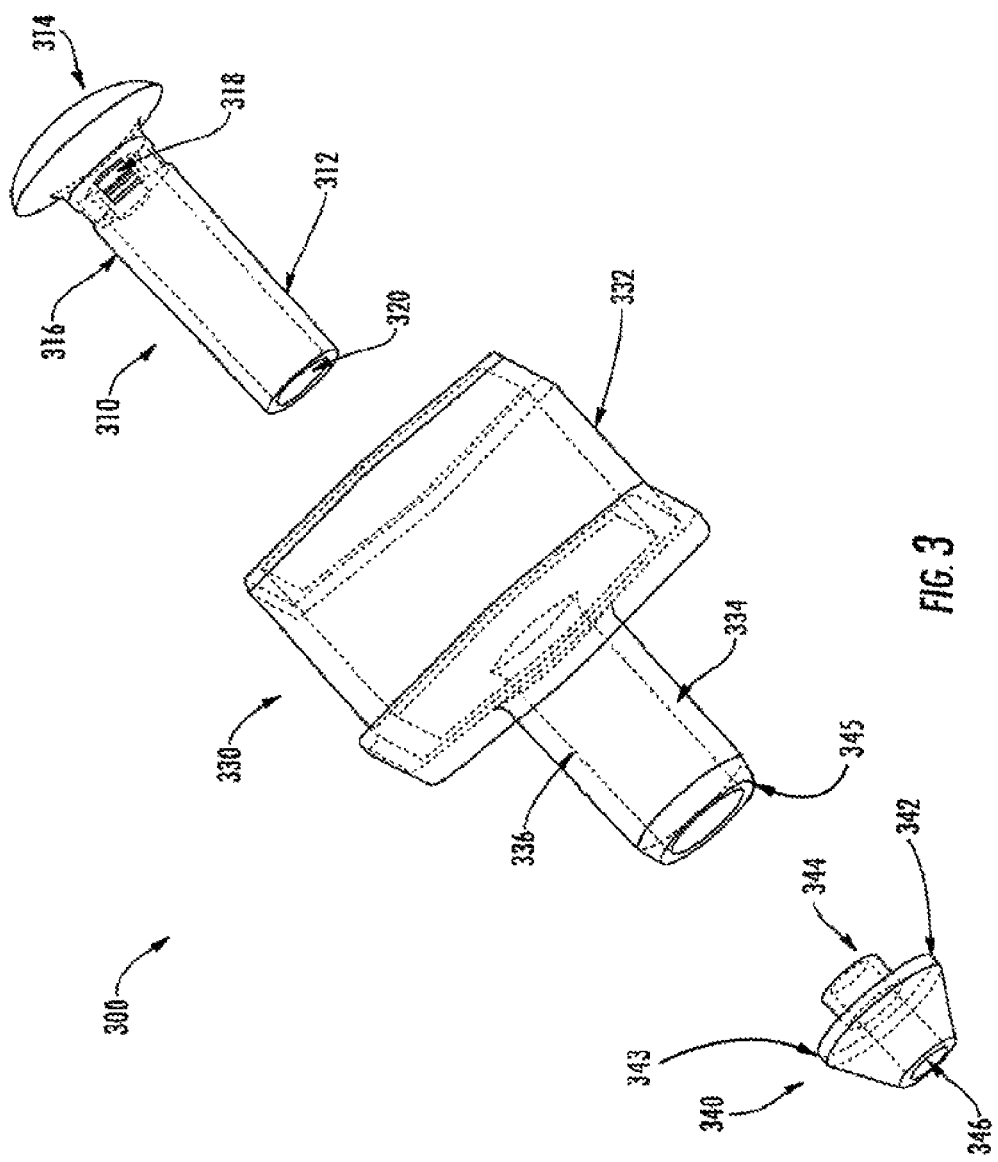
FIG. 3 is a schematic exploding view illustration showing a medical tubing valve in accordance with variations of the present invention.

Reference is now made to FIG. 3 which is a schematic exploding view illustration showing valve 300 in accordance with variations of the present invention. Valve 300 generally comprises three components: a valve stem 310, a valve body 330, and a valve tip 340.

Valve stem 310 preferably comprises an elongated hollow cylindrical portion; valve stem cylinder 312 attached to wider solid valve stem top 314. Valve stem cylinder 312 preferably has a conical surface 316. Valve stem 310 also preferably includes one or more stem inlet ports 318 that are situated below valve stem top 314, and a valve stem outlet 320. Conical surface 316 may optionally be a frustoconical surface.

Valve body 330 comprises a valve inlet chamber 332, and a central bore 334. Inlet chamber 332 is preferably shaped and sized so that its outer dimensions are slightly smaller than the inner dimensions of a drop chamber in a urinary catheter kit such as the drop chamber 110 described in FIG. 1 above or optionally any other tubing or attachment mechanism in applications where the valve 300 is employed in order to allow the tight attachment of valve body 330 to said drop chamber, tubing or attachment. This attachment is further described below.

Central bore 334 is preferably cylindrical and hollow with an inner diameter slightly wider than the outer diameter of valve stem cylinder 312. The inner surface 336 of central bore 334 preferably has a conical or frustoconical form, preferably shaped to match the conical or frustoconical surface 316 on the outer surface of stem cylinder 312. These dimensions preferably allow the insertion of valve stem 310 into valve body 330 so that the conical surface 316 of stem cylinder 312 fits snugly against the conical inner surface 336 of central bore 334.

Valve tip 340 preferably includes a tube attachment part 342, a stem insertion part 344 and valve outlet port 346. Tube attachment part 342 is preferably conically shaped and sized so that its outer dimensions are the same or slightly wider than the inner dimensions of an attachment tube in a urinary catheter kit such as the attachment tube 130 described above or optionally any other tubing or attachment mechanism in applications where the valve 300 is employed in order to allow the tight attachment of the valve to said attachment tube, or other tubing or attachment. An outermost dimension of the tube attachment part 342 is preferably wider than the diameter of central bore 334 and forms a radially enlarged shoulder 343.

Stem insertion part 344 is preferably sized to so that its outer diameter is slightly smaller than valve stem outlet 310. This enables stem insertion 344 of valve tip 340 to be attached to stem outlet 310 optionally using adhesive or ultrasonic welding so as to permanently fix it after insertion.

Figure 4:
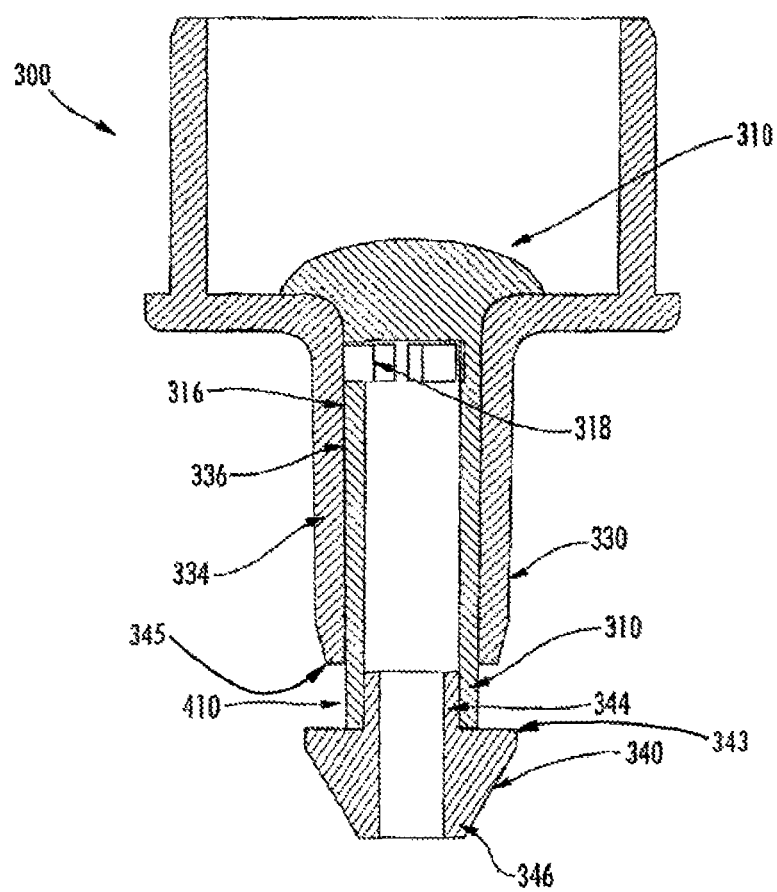
FIG. 4 is a schematic cross section view of the valve of FIG. 3 in a closed position, in accordance with variations of the present invention.
Figure 5:
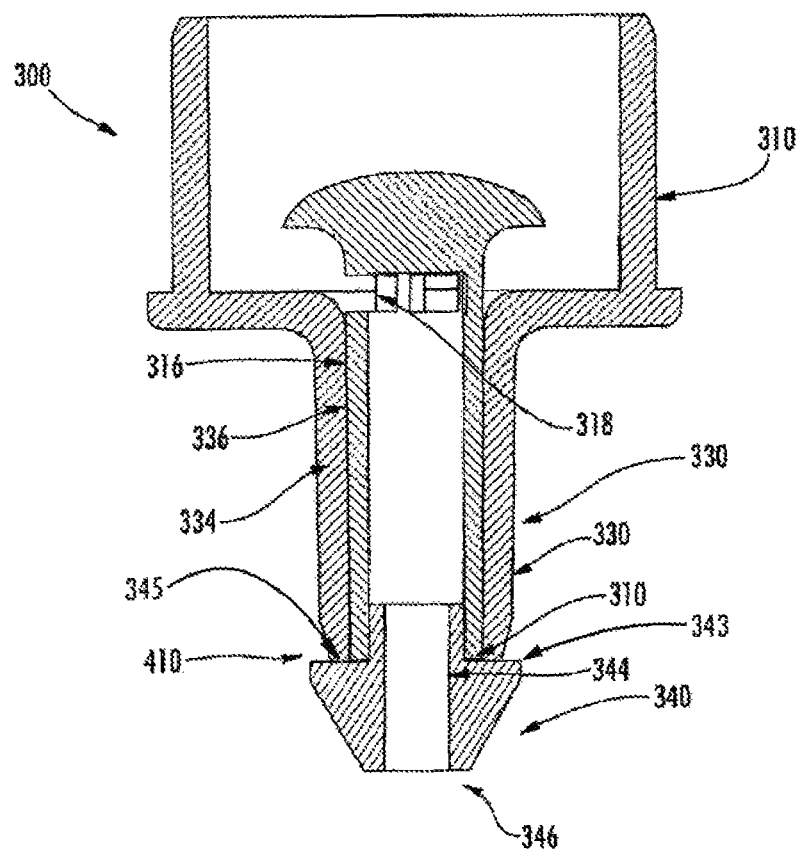
FIG. 5 is a schematic cross section view showing the valve of FIG. 3 in an open position, in accordance with variations of the present invention.

Reference is now made to FIGS. 4 and 5 that illustrate valve 300 in a closed and open position respectively, in accordance with variations of the invention.

FIG. 4 is a schematic cross section view of valve 300 of FIG. 3 in a closed position, in accordance with variations of the present invention.

As shown, the assembled valve preferably includes valve stem 310 inserted into valve body 330. Valve stem outlet 310 is attached to stem insertion 344 of valve tip 340. The assembled valve stem and valve tip can move up and down within the valve body.

When valve 300 is in a closed position, inlet port 318 is sealed against the inner surface 336 of central bore 334. Conical surface 316 of valve stem 310 is pressed against conical inner surface 336 of central bore 334 creating a light interference fit that will hold the valve closed. The conical shape of the interference fit allows the fit to be broken with relative ease. When the valve is in a closed position, a gap 410 exists between valve body 330 and the tube insertion part 342 of valve tip 340.

FIG. 5 is a schematic cross section view showing the valve 300 of FIG. 3 in an open position, in accordance with variations of the present invention. When valve 300 is in an open position, assembled valve stem 310 and valve tip 340 together move upward until the radially enlarged shoulder abuts against a bottom surface 345 of the valve body 330, closing gap 410. Inlet port 318 is not blocked by the inner surface 336 of central bore 334.

Figure 6:
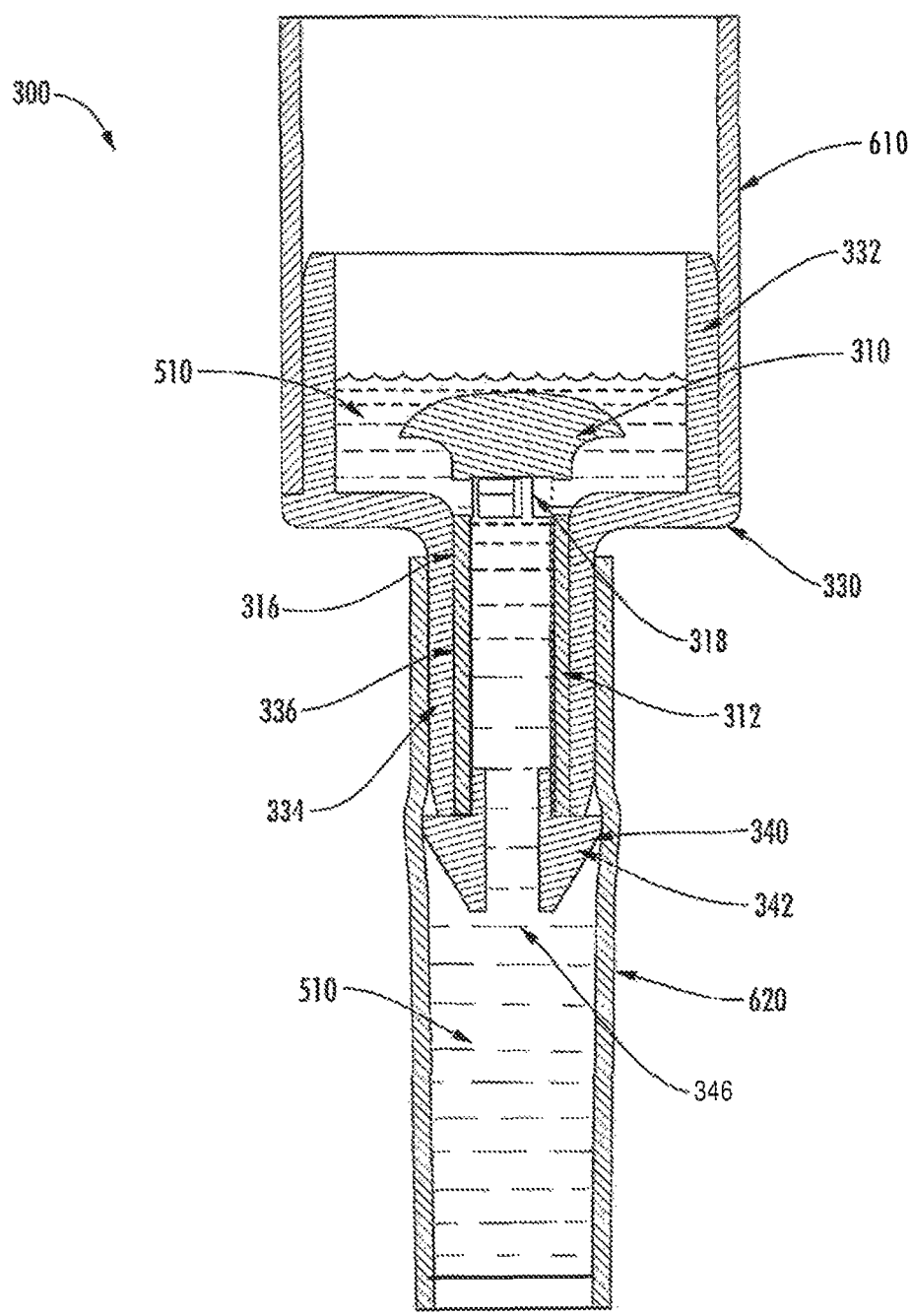
FIG. 6 is a schematic cross section view showing the valve of FIG. 3 in an open position allowing the flow of fluid, in accordance with variations of the present invention.
Figure 7:
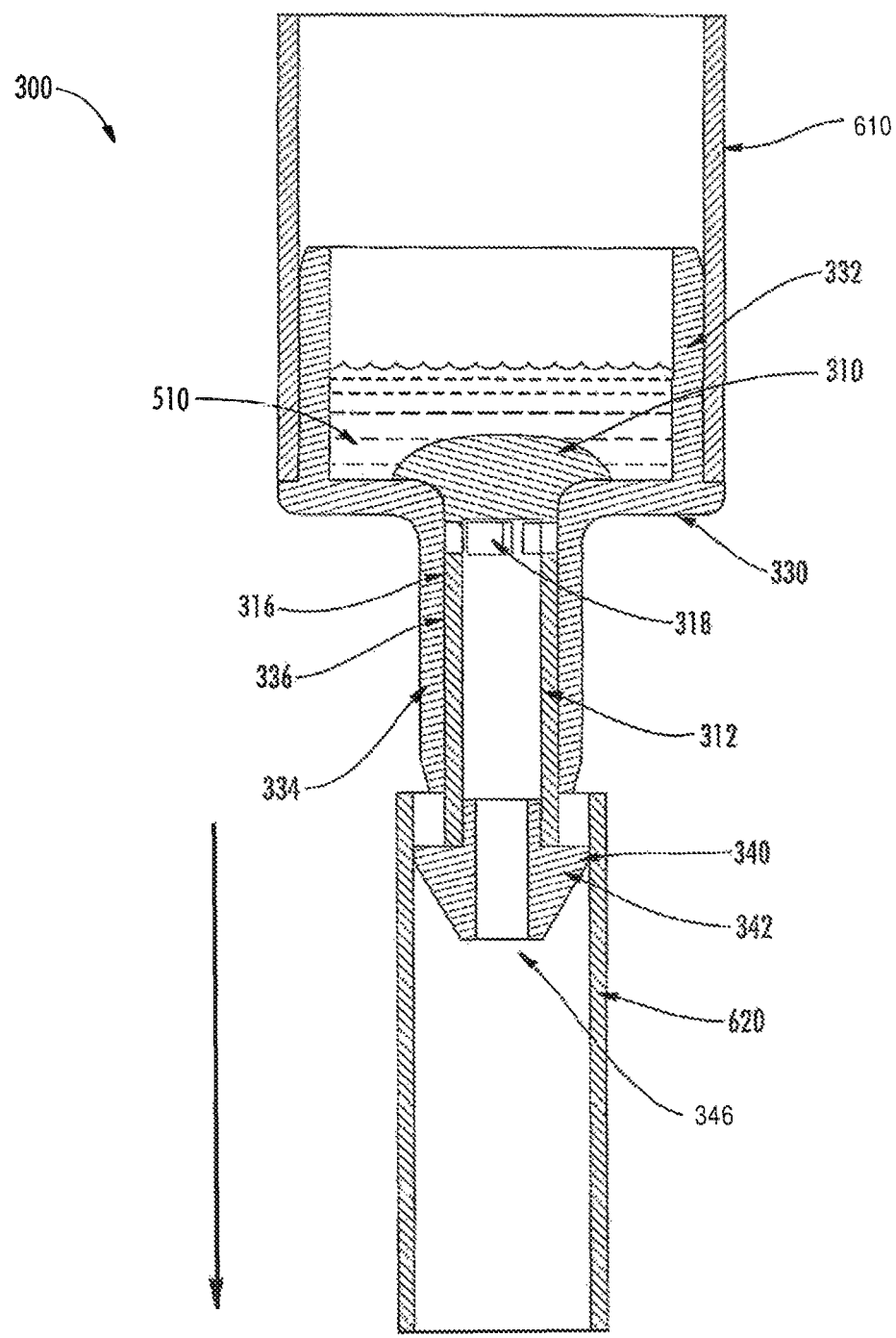
FIG. 7 is a schematic cross section view showing the valve of FIG. 3 pulled into a closed position preventing the flow of fluid, in accordance with variations of the present invention.
Figure 8:
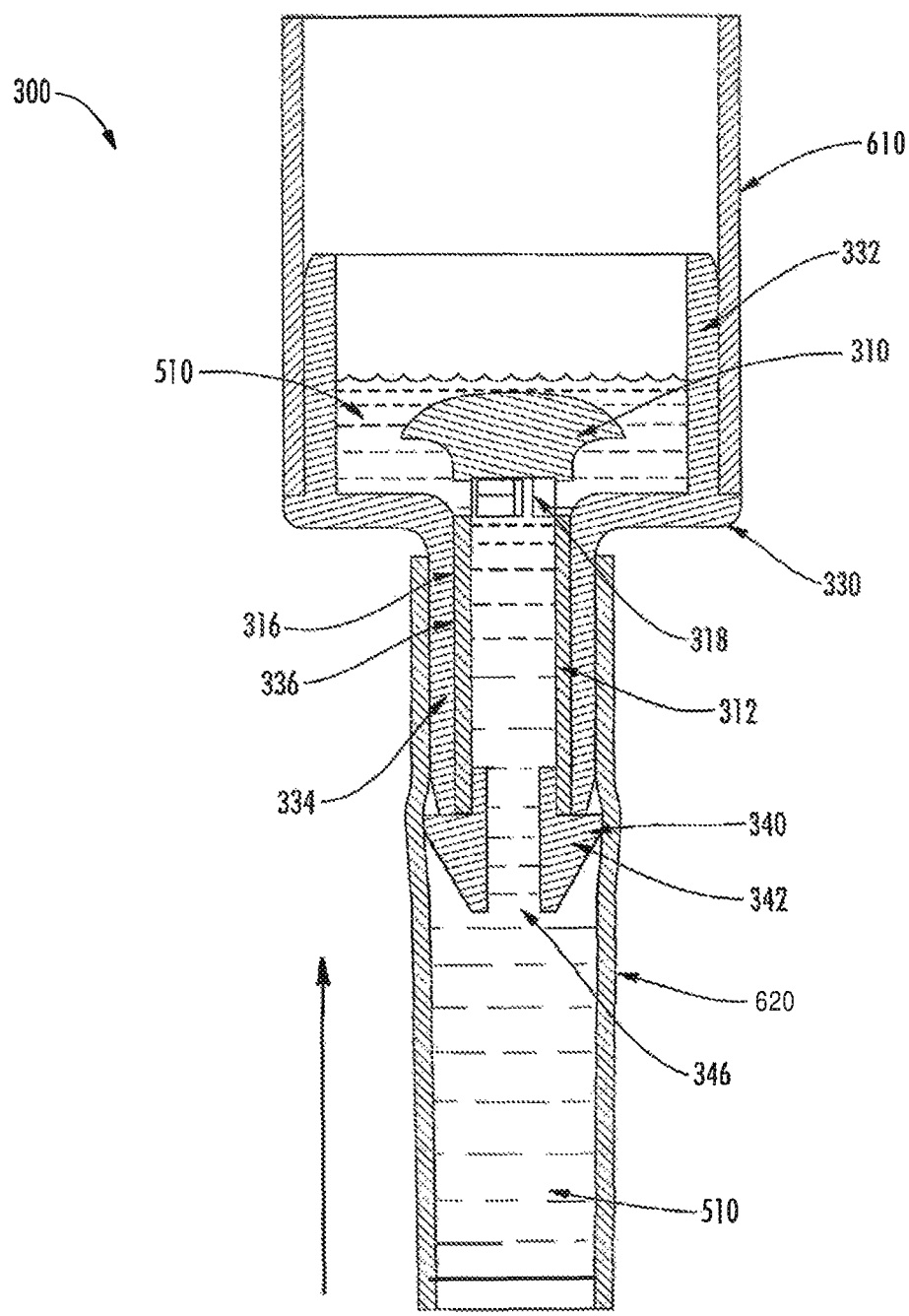
FIG. 8 is a schematic cross section view showing the valve of FIG. 3 pushed into an open position allowing the flow of fluid, in accordance with variations of the present invention.

Reference is now made to FIGS. 6, 7, and 8 that respectively illustrate fluid flow through valve 300 in an open position, valve 300 pulled into a closed position preventing fluid flow, and fluid flow through valve 300 pushed into an open position, in accordance with variations of the invention.

As shown, the valve inlet chamber 332 is preferably attached to a source of fluid, which may optionally include the drop chamber 110 of catheter assembly 100 of FIG. 1 or any other source of fluid depending on the application in which the valve is used. The attachment is made by sliding the outlet attachment 610 of the fluid source over the outside surface of the valve inlet chamber 332. As described above, the size and shape of inlet chamber 332 preferably matches that of the outlet attachment 610 in use.

The outlet of valve 300 is preferably attached to the destination of the fluid flow which may optionally include the attachment tube 130 of catheter assembly 100 of FIG. 1 or any other fluid destination depending on the application in which the valve is used. The attachment is made by sliding the attachment tube 620 of the fluid destination over the outside surface of the tube attachment port 342 and the central bore 334. As described above, the size and shape of attachment port 342 preferably matches that of the tube attachment 620 in use. The conical shape of attachment port 342 preferably eases the process of deforming tube 620 when sliding it onto the valve.

FIG. 6 is a schematic cross section view showing the valve 300 of FIG. 3 in an open position, in accordance with variations of the present invention. When valve 300 is in an open position, fluid 510 that has accumulated in valve inlet chamber 332 of valve body 330 flows through inlet port 318 and stem cylinder 312 of valve stem 310 before exiting the valve through outlet port 346 of valve tip 340. Tube 620 holds valve 300 in an open position by gripping the outer surface of central bore 334 and the outer surface of valve tip 340.

FIG. 7 is a schematic cross section view showing the valve 300 of FIG. 3 pulled into a closed position, in accordance with variations of the present invention. As tube 620 is pulled off the valve, valve tip 340 is pulled downward due to the friction against tube attachment part 342. Valve stem 310 which is attached to valve tip 340 is also pulled down causing stem inlet ports 318 to be sealed against the inner surface 336 of central bore 334 and preventing the further flow of fluids 510 accumulated in inlet chamber 332 through the valve. Conical surface 316 of valve stem 310 is pressed against conical inner surface 336 of central bore 334 creating a light interference fit that holds the valve closed.

FIG. 8 is a schematic cross section view showing the valve 300 of FIG. 3 pushed into an open position, in accordance with variations of the present invention. When an attachment tube 620 is forced onto the valve 300 by pushing it over the conical surface of attachment part 342 of valve tip 340, the valve tip is pushed upward. Valve stem 310 which is attached to valve tip 340 is also pushed upward breaking the light interference fit between conical surface 316 of valve stem 310 and conical inner surface 336 of central bore 334. Stem inlet ports 318 are pushed out of the central bore 334 allowing fluid 510 that has accumulated in inlet chamber 332 to once more enter inlet ports 318 and stem cylinder of valve stem 310, before exiting the valve through outlet port 346 of valve tip 340. Tube 620 holds valve 300 in an open position by gripping the outer surface of central bore 334 and the outer surface of valve tip 340.

The valve of the present invention aims to allow replacement of a urine bag or any other collected secreted fluids in a clean and sterile manner. When the tube is pulled off the valve of the invention, the valve closes and no flow through the valve is possible. In addition, in use, the valve prevents direct human contact with urine or with other biohazardous materials as there is no need to touch any other part other than the outer tube 620 of the collecting bag when replacing it.

No mechanism is otherwise involved in opening or closing the valve aside from sliding the attachment tube 620 on or off, thus making the mechanism provided herein simple, cheap and reliable. In addition, no special fitting or finishing is required to create the interference fit as this is provided by the matching conical inner surfaces making molding quite easy.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above described embodiments that would still be covered by the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

What is claimed is:

1. A tubing valve, comprising: a valve body; a valve stem configured to be inserted into said valve body where said valve stem has an inlet port; and a valve tip separate from said valve body and configured to be inserted and fixed into said valve stem after a first end of said valve tip is positioned inside said valve body, wherein a second end of said valve tip is conically-shaped and is configured for holding an axially-inserted tube, wherein an outermost dimension of said conically-shaped second end of said valve tip forms a radially enlarged shoulder located between said first and second tip ends, wherein said tubing valve is configured so that said outer diameter of said valve tip generally corresponds to an outer diameter of said body for slidingly receiving the tube to open upon user slindingly attaching the tube to said valve tip, causing said valve stem to move away from said valve body and to permit fluid access to said inlet port and also causing said shoulder to contact said valve body, preventing further valve opening movement of said stem in said body, and is configured to close upon the user slindingly removing the tube from said body and said valve tip, causing said shoulder of said valve stem to move toward said valve body and to block fluid access to said inlet port.

2. The valve according to claim 1, wherein said valve body further comprises a central bore, wherein said first portion of said valve stem has a greater area and a second portion having a smaller area, wherein a portion of said central bore is narrower than a second portion of said central bore, said narrower portion receiving said second portion of said valve stem and said second portion of said central bore receiving said first portion of said valve stem having said greater area.

3. The valve of claim 2, wherein upon user attachment of the tube to said first end of said valve, said valve stem having said inlet port is caused to move away from said valve body to open the valve.

4. The valve of claim 3, wherein upon said user attachment of the tube to said second end of said valve tip, said second end of said valve tip is configured to be inserted into said tube and is configured to cause said first end of said valve tip to contact said second portion of said valve stem.

5. The valve of claim 4, wherein said narrower portion of said central bore is configured to be inserted into said tube with said second end of said valve tip, thereby preventing the valve from closing when said tube is attached to the valve.

6. The valve of claim 5, wherein said second end of said valve tip is configured to move away from said valve body upon removal of said tube and hence to cause said first end of said valve tip to cease to contact said second portion of said valve stem having said inlet port, thereby closing said valve.

7. The valve of claim 1, wherein said valve stem and said central bore of said valve body each comprise complementary conical structures, such that when said tubing valve is closed, said conical structure of said valve stem having said inlet port is larger than said conical structure of said central bore, thereby blocking said inlet port.

8. A tubing valve, comprising: a valve body having a flow control mechanism including a valve stem having an inlet port configured to be inserted into said valve body and a valve tip configured to be inserted and fixed into said valve stem after a first end of said valve tip is positioned inside said valve body; a second end of said valve tip is conically shaped and is configured for holding an axially inserted tube, wherein an outermost dimension of said second end of said valve tip forms a radially enlarged shoulder located between said first and second tip ends; said tubing valve is opened upon slidingly attaching the tube to said valve tip and to said valve body, causing a radially enlarged first portion of said valve stem to move away from said valve body and to permit fluid access to said inlet port, and said radially enlarged shoulder on said tip to contact said valve body, and closed upon removing the tube from said valve tip and said valve body, causing said radially enlarged first portion of said valve stem to move toward said valve body and to block fluid access to said inlet port, a direct fit between said valve stem and a complementary bore in said valve body prevents unwanted fluid access to said inlet port when said valve is closed.

9. The valve according to claim 8, wherein said valve is configured to be used in low and medium pressure applications.

10. The valve according to claim 8, further comprising a medical tube attached to said valve.

* * * * *